US012721589B2

(12) United States Patent
Bunn

(10) Patent No.: US 12,721,589 B2
(45) Date of Patent: Sep. 1, 2026

(54) ARTIFICIAL INTELLIGENCE SYSTEM FOR DETERMINING DRUG USE THROUGH MEDICAL IMAGING

(71) Applicant: Ultrasound AI, Inc., Highlands Ranch, CO (US)

(72) Inventor: Robert S Bunn, Highlands Ranch, CO (US)

(73) Assignee: Ultrasound AI, Inc., Greenwood Village, CO (US)

( * ) Notice: Subject to any disclaimer, the term of this patent is extended or adjusted under 35 U.S.C. 154(b) by 0 days.

(21) Appl. No.: 18/431,291

(22) Filed: Feb. 2, 2024

(65) Prior Publication Data

US 2024/0197287 A1 Jun. 20, 2024

Related U.S. Application Data

(63) Continuation-in-part of application No. 17/573,246, filed on Jan. 11, 2022, now Pat. No. 11,969,289, (Continued)

(51) Int. Cl.

*A61B 5/00* (2006.01)
*A61B 8/00* (2006.01)
(Continued)

(52) U.S. Cl.

CPC .............. *A61B 8/0866* (2013.01); *A61B 8/06* (2013.01); *A61B 8/0875* (2013.01); (Continued)

(58) Field of Classification Search

CPC ......... A61B 8/06; A61B 8/0883; A61B 8/467; A61B 8/488; A61B 8/0875; A61B 8/0866;
(Continued)

(56) References Cited

U.S. PATENT DOCUMENTS

| | | | |
|---|---|---|---|
| 8,828,981 | B2 | 9/2014 | Creasy et al. |
| 10,650,929 | B1 | 5/2020 | Beck et al. |

(Continued)

FOREIGN PATENT DOCUMENTS

| | | | |
|---|---|---|---|
| CN | 110613480 | A | 12/2019 |
| IN | 201941040741 | A | 4/2021 |

(Continued)

OTHER PUBLICATIONS

Office Action Issued in related Chinese Patent Application No. 202180043378.8 issued Dec. 28, 2023, 27 pages.

(Continued)

*Primary Examiner* — Joel F Brutus
(74) *Attorney, Agent, or Firm* — David J. Thibodeau; VLP Law Group LLP

(57) ABSTRACT

Systems and methods for establishing a patient's pharmaceutical use are provided. A neural network is trained on a dataset of medical images, such as ultrasound images, that are tagged with information concerning the use of the pharmaceutical by people who were imaged to produce the medical images. The trained neural network can then be provided with medical images of a patient, and the neural network can then make a determination as to the patient's pharmaceutical use.

32 Claims, 2 Drawing Sheets

Related U.S. Application Data which is a continuation of application No. PCT/US2021/038164, filed on Jun. 20, 2021, and a continuation of application No. 17/352,290, filed on Jun. 19, 2021, now Pat. No. 11,266,376.

(60) Provisional application No. 63/443,169, filed on Feb. 3, 2023, provisional application No. 63/041,360, filed on Jun. 19, 2020.

(51) Int. Cl.
*A61B 8/06* (2006.01)
*A61B 8/08* (2006.01)
*G06T 7/00* (2017.01)
*G06T 7/20* (2017.01)
*G16H 10/60* (2018.01)
*G16H 30/20* (2018.01)
*G16H 30/40* (2018.01)
*G16H 50/20* (2018.01)

(52) U.S. Cl.
CPC ............ *A61B 8/0883* (2013.01); *A61B 8/467* (2013.01); *A61B 8/488* (2013.01); *G06T 7/0016* (2013.01); *G06T 7/20* (2013.01); *G16H 10/60* (2018.01); *G16H 30/20* (2018.01); *G16H 30/40* (2018.01); *G16H 50/20* (2018.01); *G06T 2207/10132* (2013.01); *G06T 2207/20081* (2013.01); *G06T 2207/30008* (2013.01); *G06T 2207/30044* (2013.01); *G06T 2207/30048* (2013.01); *G06T 2207/30104* (2013.01)

(58) Field of Classification Search
CPC . G06T 2207/10132; G06T 2207/20081; G06T 2207/30008; G06T 2207/30044; G06T 2207/30048
See application file for complete search history.

(56) References Cited

U.S. PATENT DOCUMENTS 11,266,376 B2 3/2022 Bunn
11,969,289 B2 4/2024 Bunn
12,318,249 B2 6/2025 Bunn
12,369,883 B2 7/2025 Bunn
2004/0236193 A1 11/2004 Sharf
2006/0241510 A1 10/2006 Halperin et al.
2009/0093717 A1 4/2009 Carneiro et al.
2009/0169074 A1 7/2009 Avinash et al.
2010/0312115 A1 12/2010 Dentinger
2011/0248818 A1 10/2011 Hashim-Waris
2012/0135427 A1 5/2012 Kypros et al.
2014/0018678 A1 1/2014 Donnelly et al.
2014/0089004 A1 3/2014 Frey et al.
2015/0148657 A1 5/2015 Shashar et al.
2015/0342560 A1 12/2015 Davey et al.
2016/0071266 A1* 3/2016 Srivastava ............ G06T 7/0016 382/130
2016/0228505 A1 8/2016 Stossel et al.
2016/0340407 A1* 11/2016 Hodi .................... C12Q 1/6886
2017/0000683 A1* 1/2017 Samec ................... A61B 3/066
2017/0086785 A1 3/2017 Bjaerum
2017/0091402 A1 3/2017 Salafia et al.
2017/0216335 A1 8/2017 Mangano
2017/0357844 A1 12/2017 Comaniciu et al.
2018/0032666 A1 2/2018 Sun et al.
2018/0153504 A1* 6/2018 Herickhoff ........... A61B 8/4472
2018/0247410 A1* 8/2018 Madabhushi ............. G06T 7/11
2019/0008674 A1 1/2019 Myers et al.
2019/0021698 A1 1/2019 Raghvan et al.
2019/0034590 A1 1/2019 Oren et al.
2019/0154704 A1 5/2019 Davis et al.
2019/0209116 A1 7/2019 Sjostrand et al.
2019/0246904 A1 8/2019 Kim et al.
2019/0251638 A1 8/2019 Braz et al.
2019/0367987 A1 12/2019 Hamamah et al.
2020/0005899 A1 1/2020 Nicula et al.
2020/0005901 A1 1/2020 Cohen et al.
2020/0022674 A1 1/2020 Egorov
2020/0035362 A1 1/2020 Abou et al.
2020/0069292 A1* 3/2020 Abolmaesumi ...... A61B 8/5207
2020/0077947 A1 3/2020 Shi et al.
2020/0147006 A1 5/2020 Charney et al.
2020/0149110 A1 5/2020 Targan et al.
2020/0168310 A1 5/2020 Westin et al.
2020/0170614 A1 6/2020 Kim et al.
2021/0068905 A1 3/2021 Quaid et al.
2021/0090254 A1 3/2021 Gong et al.
2021/0118559 A1 4/2021 Lefkofsky
2021/0128115 A1 5/2021 Mapiye et al.
2021/0217166 A1 7/2021 Graule et al.
2021/0287513 A1 9/2021 Mazar et al.
2021/0307702 A1 10/2021 Moon
2021/0393235 A1 12/2021 Bunn
2022/0028551 A1 1/2022 Jordan et al.
2022/0067922 A1 3/2022 Yu
2022/0133260 A1 5/2022 Bunn
2022/0133280 A1 5/2022 Urabe et al.
2022/0164635 A1 5/2022 Johansen et al.
2022/0192501 A1 6/2022 Shuler
2022/0328189 A1 10/2022 Zhou et al.
2022/0400963 A1 12/2022 Bucklet et al.
2023/0172580 A1 6/2023 Bunn et al.
2024/0173011 A1 5/2024 Bunn
2024/0173012 A1 5/2024 Bunn
2024/0215945 A1 7/2024 Bunn
2025/0275747 A1 9/2025 Bunn

FOREIGN PATENT DOCUMENTS

JP 2018-140172 A 9/2018
KR 10-2020-0013161 A 2/2020
WO 2020/061590 A1 3/2020
WO 2020107023 A1 5/2020

OTHER PUBLICATIONS

PCT/US21/38164 International Search Report and Written Opinion, mailed Sep. 30, 2021.
PCT/US23/011845 International Search Report and Written Opinion, mailed Apr. 27, 2023.
PCT/US24/014349 International Search Report and Written Opinion, mailed May 7, 2024.
PCT/US24/019803 International Search Report and Written Opinion, mailed Jun. 17, 2024.
PCT/US24/014353 International Search Report and Written Opinion, mailed May 7, 2024.
PCT/US24/014356 International Search Report and Written Opinion, mailed May 9, 2024.
Kuo et al., "Automation of the kidney function prediction and classification through ultrasoundbased kidney imaging using deep learning." In: npj Digital Medicine vol. 2, Article No. 29 (2019), [onlinel [retrieved on Apr. 17, 2024 (Apr. 17, 2024)] Retrieved from the Internet < URL: https://www.nature.com/articles/s41746-019-0104-2#ethlcs>.
CN 202180043378.8, Response to first office action issued Dec. 28, 2023, dated May 10, 2024.
CN 202180043378.8, Rejection Decision issued May 18, 2024.
CN 202180043378.8, Response to Rejection Decision iissued May 18, 2024, dated Aug. 19, 2024.
EP 21825348.2 EESR Issued Jun. 18, 2024.
Oelze et al., "Review of Quantitative Ultrasound: Envelope Statistics and Backscatter Coefficient Imaging and Contributions to Diagnostic Ultrasound", IEEE Transactions on Ultrasonics, Ferroelectrics, and Frequency Control, IEEE, USA, vol. 63, No. 2, Feb. 1, 2016 (Feb. 1, 2016), pp. 336-351, XP011597293, ISSN: 0885-3010, DOI: 10.1109/TUFFC.2015.2513958 [retrieved on Jan. 29, 2016].

(56) References Cited

OTHER PUBLICATIONS

Suff Natalie et al: “The prediction of preterm delivery: What is new?”, Seminars in Fetal and Neonatal Medicine, Elsevier, GB, vol. 24, No. 1, Sep. 28, 2018 (Sep. 28, 2018), pp. 27-32, XP085591331, ISSN: 1744-165X, DOI: 10.1016/J.SINY.2018.09.006.
Pizzella Stephanie et al: “Evolving cervical imaging technologies to predict preterm birth”, Seminars in Immunopathology, Springer Berlin Heidelberg, Berlin/Heidelberg, vol. 42, No. 4, Jun. 10, 2020 (Jun. 10, 2020), pp. 385-396, XP037251810, ISSN: 1863-2297, DOI: 10.1007/S00281-020-00800-5 [retrieved on Jun. 10, 2020].
JP 2022-574786, Notice of Reasons for Refusal, Issued Sep. 3, 2024.
KR 10-2023-7000075, Office Action, Issued Oct. 21, 2024.
EP 21825348.2, Response to EESR, filed Dec. 30, 2024.
JP 2022-574786, Response to Notice of Reasons for Refusal, Issued Sep. 3, 2024, filed Nov. 19, 2024.
KR 10-2023-7000075, Response to Office Action, Issued Oct. 21, 2024, filed Dec. 23, 2024.
Office Action dated Feb. 4, 2025 regarding JP2022-574786.
CN 202180043378.8, Response to Rejection Decision issued May 18, 2024, dated Aug. 19, 2024.
International Preliminary Report on Patentability received for PCT Patent Application No. PCT/US2021/038164, mailed on Dec. 29, 2022, 9 pages.
International Preliminary Report on Patentability received for PCT Patent Application No. PCT/US2023/011845, mailed on Aug. 8, 2024, 12 pages.
Andrea Campagner, #., Luisa Agnello, #., Carobene, A., Padoan, A., Del Ben, F., Locatelli, M., . . . Marcello Ciaccio, #. (2025). Complete Blood Count and Monocyte Distribution Width-Based Machine Learning Algorithms for Sepsis Detection: Multicentric Development and External Validation Study. J. Med. Internet Res., 40009841. Retrieved from https://pubmed.ncbi.nlm.nih.gov/40009841.
Beauchamp, N. J., Bryan, R. N., Bui, M. M., Krestin, G. P., McGinty, G. B., Meltzer, C. C., & Neumaier, M. (2023). Integrative diagnostics: the time is now—a report from the International Society for Strategic Studies in Radiology. Insights Imaging, 14(1), 1-13. doi: 10.1186/s13244-023-01379-9.
C-AILM https://ifcc.org/ifcc-emerging-technologies-division/etd-committees/wg-aigd/.
C-ID https://www.eflm.eu/site/who-we-are/divisions/science-division/fu/c-integrative-diagnostics.
Cesselli, D., Ius, T., Isola, M., Del Ben, F., Da Col, G., Bulfoni, M., Skrap, M. (2019). Application of an Artificial Intelligence Algorithm to Prognostically Stratify Grade II Gliomas. Cancers, 31877896. Retrieved from https://pubmed.ncbi.nlm.nih.gov/31877896.
Da Col, G., Del Ben, F., Bulfoni, M., Turetta, M., Gerratana, L., Bertozzi, S., . . . Cesselli, D. (2022). Image Analysis of Circulating Tumor Cells and Leukocytes Predicts Survival and Metastatic Pattern in Breast Cancer Patients. Front. Oncol., 35223462. Retrieved from https://pubmed.ncbi.nlm.nih.gov/35223462.
Del Ben, F. (2025). Beyond test results: the strategic importance of metadata for the integration of AI in laboratory medicine. Clin. Chern. Lab. Med., 39846365. Retrieved from https://pubmed.ncbi.nlm.nih.gov/39846365.
Del Ben, F., Biasizzo, J., & Curcio, F. (2019). A fast, nondestructive, low-cost method for the determination of hematocrit of dried blood spots using image analysis. Clin. Chern. Lab. Med., 30179847. Retrieved from https://pubmed. ncbi.nl m.nih.gov/30179847.
Del Ben, F., Da Col, G., Cobarzan, D., Turetta, M., Rubin, D., Buttazzi, P., & Antico, A. (2023). A fully interpretable machine learning model for increasing the effectiveness of urine screening. Am. J. Clin. Pathol., 37658807. Retrieved from https://pubmed.ncbi.nlm.nih.gov/37658807.
Fabris, M., Del Ben, F., Sozio, E., Beltrami, A. P., Cifii, A., Bertolino, G., . . . Curcio, F. (2022). Cytokines from Bench to Bedside: A Retrospective Study Identifies a Definite Panel of Biomarkers to Early Assess the Risk of Negative Outcome in COVID-19 Patients. Int. J. Mol. Sci., 35563218. Retrieved from https://pubmed.ncbi.nlm.nih.gov/35563218.
Soldati, G., Del Ben, F., Brisotto, G., Biscontin, E., Bulfoni, M., Piruska, A., . . . Mea, V. D. (2018). Microfluidic droplets 1 2 content classification and analysis through convolutional neural networks in a liquid biopsy workflow. Am. J. Transl. Res., 30662646. Retrieved from https://pubmed.ncbi.nlm.nih.gov/30662646.
Sorace, J., Aberle, D. R., Elimam, D., Lawvere, S., Tawfik, 0., & Wallace, W. D. (2012). Integrating pathology and radiology disciplines: an emerging opportunity? BMC Med., 10(1), 1-6. doi: 10.1186/1741-7015-10-100.
Wild, R., Sozio, E., Margiotta, R. G., Dellai, F., Acquasanta, A., Del Ben, F., . . . Laio, A. (2024). Maximally informative feature selection using Information Imbalance: Application to COVID-19 severity prediction. Sci. Rep., 38730063. Retrieved from https://pubmed.ncbi.nlm.nih.gov/38730063.
Diniz Pedro H. et al.: “Deep Learning Strategies for Ultrasound in Pregnancy”, EMJ Reproductive Health, (Aug. 25, 2020), pp. 73-80, XP093365490, ISSN: 2059-450X, DOI: 10.33590/emjreprohealth/20-00100 Retrieved from the Internet: URL:https://pmc.ncbi.nlm.nih.gov/articles/PMC7590498/pdf/nihms-1638999.pdf.
Wang Qian et al.: “Smart Ultrasound Imaging and Perinatal, Preterm and Paediatric Image Analysis” First International Workshop, SUSI 2019, and 4th International Workshop, PIPPI 2019, Held in Conjunction with MICCAI 2019, Shenzhen, China, Oct. 13 and 17, 2019, Proceedings“”, Jan. 1, 2019 (Jan. 1, 2019), Springer International Publishing, XP093365880, ISSN: 0302-9743, ISBN: 978-3-030-32875-7, vol. 11798, pp. 1-201, Retrieved from the Internet.

* cited by examiner

ARTIFICIAL INTELLIGENCE SYSTEM FOR DETERMINING DRUG USE THROUGH MEDICAL IMAGING

CROSS-REFERENCE TO RELATED APPLICATIONS

This application is a Continuation-In-Part of U.S. patent application Ser. No. 17/573,246 filed on Jan. 11, 2022 which is a Continuation of U.S. patent application Ser. No. 17/352,290 filed Jun. 19, 2021, now U.S. Pat. No. 11,266,376, which claims the benefit of U.S. Provisional Patent Application No. 63/041,360 filed on Jun. 19, 2020; U.S. patent application Ser. No. 17/573,246 also is a Continuation of International Application PCT/US21/38164 filed on Jun. 20, 2021. This application also claims the benefit of U.S. Provisional Patent Application No. 63/443,169 filed Feb. 3, 2023. The disclosures of each of the aforementioned patent applications are incorporated herein by reference.

BACKGROUND OF THE INVENTION

Field of the Invention

The invention pertains to the field of medical imaging and artificial intelligence, specifically focusing on using non-invasive medical imaging techniques and advanced machine learning algorithms to determine a patient's medication use, promising to enhance drug detection precision and efficiency in healthcare and related sectors.

Description of the Prior Art

Traditional methods of drug use detection have primarily consisted of invasive blood or urine tests for determining a patient's medication use. These well-established techniques have been the standard for detecting drug presence in a patient's system. However, they come with inherent drawbacks such as invasiveness, time-consuming processes, and potential discomfort for patients. Furthermore, these methods do not provide real-time or continuous monitoring, which can limit their effectiveness in dynamic healthcare environments where timely interventions are critical.

SUMMARY

Ultrasound, and optionally other medical imaging techniques, are used to generate determinations regarding the detection of pharmaceutical drug usage in a patient's system. These determinations involve identifying the presence or absence of specific pharmaceutical drugs based on the medical images. The determinations provide a novel method for early detection and monitoring of drug usage.

Various embodiments include using medical images, e.g., ultrasound images, as an input to a machine learning system configured to produce quantitative or qualitative determinations based on those images. These machine learning systems may use regression, a classification approach, and/or other machine learning algorithms. For example, any regression algorithm that outputs ranges may be used, e.g., quantile regression. In some embodiments, multiple algorithms are combined in a single AI in a unique approach.

Various embodiments also include preprocessing of images and/or pre-training of machine learning systems. For example, preprocessing of images has been found to be useful where medical images are of poor or variable quality or of variable size, e.g., where the images are ultrasound images.

Various embodiments of the invention comprise a medical diagnostic system configured to detect pharmaceutical drug usage, the system comprising: an image storage configured to store medical images, the medical images including relevant anatomical structures or markers; image analysis logic configured to provide determinations of ongoing pharmaceutical drug usage based on the medical images; a user interface configured to provide at least the determinations of drug usage to a user; and a microprocessor configured to execute at least a part of the image analysis logic. The image analysis logic optionally comprises logic configured to identify specific pharmaceutical drugs in the patient's system based on the medical images.

Various embodiments of the invention include a method of generating quantitative or qualitative determinations of pharmaceutical drug usage. An exemplary method comprising: obtaining a set of medical images; analyzing the medical images using a machine learning system to produce quantitative determinations including the presence or absence of pharmaceutical drugs in the patient's system; and providing the quantitative determinations to a user.

Various embodiments of the invention include a method of training a medical determination system, the method comprising: receiving a plurality of medical images; optionally filtering the images; optionally classifying the images according to the views or features included within the images; optionally pretraining a neural network to recognize features within the images or types of images; training the neural network to provide quantitative or qualitative determinations regarding pharmaceutical drug usage, the determinations including the presence or absence of pharmaceutical drugs; and optionally testing the trained neural network to determine the accuracy of the quantitative or qualitative determinations.

Various embodiments of the invention include a method of acquiring medical images for training a neural network, the method comprising: creating a dataset of medical images; identifying relevant medical images in the dataset; and using the medical images to train a neural network to generate determinations that the medical images are indicative of ongoing pharmaceutical drug usage, the determinations including the presence or absence of pharmaceutical drugs.

DETAILED DESCRIPTION

The systems and methods disclosed herein offer either quantitative or qualitative assessments of a patient's past or current pharmaceutical consumption. Here, a "quantitative determination" encompasses elements such as probability assessments, classifications into various pharmaceutical categories, or estimates of pharmaceutical dosage. In the case of dosage estimation, it might be expressed, for example, as estimated milligrams consumed per specific time duration. The advantage of quantitative determination lies in its capacity to provide considerably more actionable information compared to a mere qualitative classification.

Figure 1:
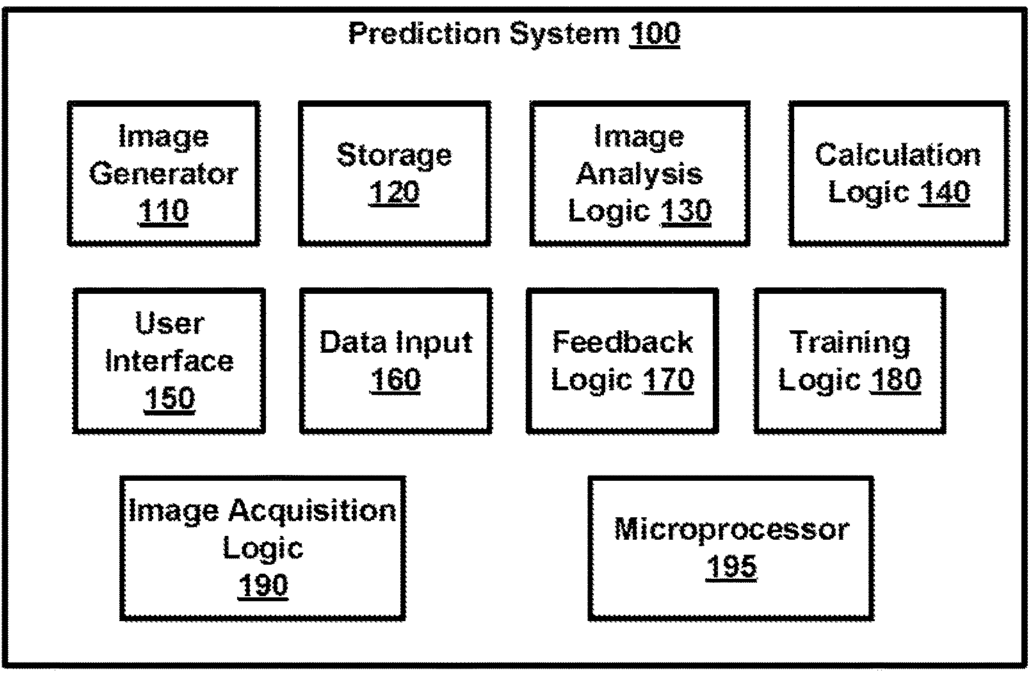
FIG. 1 illustrates medical diagnostic systems configured to determine chemical compound use, according to various embodiments of the invention.

FIG. 1 depicts a medical Determination System 100, tailored for pharmaceutical usage determination, in accordance with various embodiments of the invention. Determination System 100 may comprise multiple devices, including an ultrasound system and a computing device geared towards image processing. Optionally, the components of the Determination System 100 communicate with each other and with external devices through a communication network like the Internet.

Image processing, aimed at generating determinations, encompasses the generation of estimates pertaining to the usage of specific pharmaceutical drugs or classes of pharmaceutical drugs-both past and present. These estimates can be presented as absolute or relative probabilities and may incorporate a temporal component. For instance, an estimate could signify a 66% likelihood that a patient has previously utilized the drug Amoxicillin but is not currently doing so.

Determination System 100 incorporates an optional Image Generator 110 responsible for producing medical images. Image Generator 110 may include a conventional ultrasound system or another imaging mechanism, configured to deliver images to other components within Determination System 100 for subsequent processing, such as via a computer network. In various embodiments, Image Generator 110 comprises a system that combines an image generation device with one or more elements of Determination System 100. For instance, Image Generator 110 can consist of an ultrasound device equipped with Storage 120, Image Analysis Logic 130, User Interface 150, and Feedback Logic 170, as discussed in greater detail elsewhere in this document. Image Generator 110 may also encompass diverse imaging technologies, such as radiographic (e.g., X-rays), magnetic resonance, nuclear, ultrasound, elastography, photoacoustic, tomography, echocardiography, magnetic particle imaging, spectroscopic (e.g., near-infrared), or similar devices and techniques. It should be noted that in this disclosure, references to ultrasound images are by way of example, and images from any of these other imaging techniques can be readily substituted for ultrasound images in these descriptions.

In some embodiments, various components of Determination System 100 are closely integrated with or housed within the Image Generator 110. To illustrate, consider Image Generator 110, which might encompass an ultrasound machine, housing Image Analysis Logic 130. This setup is adept at providing real-time feedback through Feedback Logic 170, effectively guiding the acquisition of ultrasound data and images.

In some embodiments, Image Generator 110 may involve a sound source, a sound detector, and accompanying logic, all orchestrated to generate ultrasound images based on the sounds detected by the sensor. Image Generator 110 is designed to adapt the generation of these ultrasound images based on feedback received from Image Analysis Logic 130. A practical example of this adaptability involves fine-tuning the sound generation, focus, and processing parameters to enhance the detection of blood perfusion in the minute lung capillaries. Such adjustments respond to cues from Image Analysis Logic 130, which might signal that images containing such information would yield more accurate determinations and estimates.

It's important to note that Image Generator 110 becomes an optional component in scenarios where externally acquired images are fed into Determination System 100, or in cases where raw imaging data forms the basis for determinations. For instance, in embodiments where raw ultrasound (sonogram) data is processed to generate medical assessments, Image Generator 110 may be excluded. In some configurations, images and/or raw data are relayed to Determination System 100 via a communication network, such as the Internet. The imagery produced by Image Generator 110 could encompass a sequence illustrating the dynamic movements of a beating heart. This sequence might reveal details like blood flow patterns, capillary perfusion, heartbeat rhythm, and more. It can even incorporate Doppler information, providing insights into the direction and velocity of these movements.

Determination System 100 also includes Storage 120. This component contains digital memory capabilities for storing an array of data types. Its storage capacity can accommodate raw sensor data, medical images, medical records, executable code (logic), neural networks, and other related data. For instance, it can house raw sensor data captured by a photon or acoustic detector, a dataset instrumental in generating images like X-rays or ultrasound scans. Storage 120, as discussed throughout this document, comprises memory circuits and data structures designed to manage and store the mentioned data categories. When dealing with ultrasound images, these images may optionally be configured at 600×600 pixels, optionally encompassing randomly selected crops of 400×400 pixels, which can be used in the training and determinations outlined herein. The term "ultrasound images" in this context may also encompass three-dimensional renderings created from ultrasound data.

In certain embodiments, Storage 120 is designed with circuits for the storage of ultrasound images acquired from patients. These ultrasound images can be collected in one or more separate acquisition sessions. For instance, during the first session, a sonographer might gather an initial set of ultrasound images, and subsequently, a second set of images may be procured in a subsequent session taking place at intervals of at least 1, 2, 5, 7, 15, 21, 30, 60, 90, or 365 days, or within any range between these durations. The ultrasound images for a particular patient may span over a duration encompassing any of the mentioned timeframes. In some instances, a patient could undergo weekly ultrasound sessions. These ultrasound images may encompass Doppler data and even sequences of images (e.g., videos) illustrating the motion of various anatomical structures. Examples include images that reveal heartbeats or blood flow, and they may also incorporate data pertaining to the density of tissues, fluids, or bone. Images deemed valuable for making pharmaceutical use determinations encompass a broad spectrum, such as those depicting heart rate, liver condition, uterine status, intestinal health, femur and humerus structure, endometrial features (e.g., thickness and vascularization), kidney function, placental status, adnexa assessment, and so forth.

Determination System 100 further contains Image Analysis Logic 130. It is useful in providing either quantitative or qualitative determinations regarding a patient's past or current pharmaceutical use, derived from the ultrasound images and optionally supplemented by clinical data. These determinations come in various formats. For instance, these determinations might incorporate estimates that encompass a wide array of patient-specific factors, such as potential co-morbidities.

In some embodiments, Image Analysis Logic 130 comprises two distinct logic components. The first logic is designed to ascertain whether a patient has previously used a pharmaceutical based on the ultrasound images, while the second logic is tasked with determining if a patient is currently utilizing a pharmaceutical based on the same set of ultrasound images. For example, the first logic could analyze ultrasound images to identify past pharmaceutical usage at the time the images were generated, while the second logic focuses on pinpointing the timeframe during which this pharmaceutical was previously employed. Both the first and second logic components can be housed within the same machine learning system for cohesive analysis.

Image Analysis Logic 130 exhibits adaptability when selecting machine learning algorithms for its calculations. For instance, in some embodiments, Image Analysis Logic 130 is configured to employ a regression algorithm, such as quantile regression, to furnish determinations about pharmaceutical usage and optionally even estimate specific dosage levels. These regression methods predict a range within which the actual answer is likely to fall, as opposed to a single point value. Any regression system capable of predicting ranges rather than specific values may be employed in Image Analysis Logic 130. This use of a range-based estimation helps to prevent overfitting of the data and proves valuable when the ultrasound images used for training may have mislabeled attributes. Image Analysis Logic 130 typically bases determinations and estimates on sets of ultrasound images, rather than relying on the analysis of a single ultrasound image.

In alternative embodiments, Image Analysis Logic 130 is programmed to determine current or previous pharmaceutical usage utilizing classification algorithms. These classifications can include categories such as "No use," "Previous use," "Current use," or even "Abuse," among others. When classification algorithms are deployed, a "label smoothing" function may be applied. This smoothing function is particularly useful because certain training images may contain incorrect labels due to human error at the time of ultrasound image generation. The smoothing function may take a specific form, possibly involving epsilon (ε) values of 0.05, 0.1, 0.3, or even greater.

Sample Label Smoothing:

Instead of using one-hot encoded vector, a noise distribution u(y|x) is introduced. The new ground truth label for data (xi, yi) becomes:

$$p'(y \mid x_i) = (1-\varepsilon)p(y \mid x_i) + \varepsilon u(y \mid x_i) = \begin{cases} 1-\varepsilon+\varepsilon u(y \mid x_i) & \text{if } y = y_i \\ \varepsilon u(y \mid x_i) & \text{otherwise} \end{cases}$$

Where ε is a weight factor, ε∈[0, 1], and note $\sum_{y=1}^{K} p'(y \mid x_i)=1$ This new ground truth label is used as a replacement for the one-hot encoded ground-truth label in a loss function.

$$L' = -\sum_{i=1}^{n}\sum_{y=1}^{K} p'(y \mid x_i)\log q_\theta(y \mid x_i) = -\sum_{i=1}^{n}\sum_{y=1}^{K}[(1-\varepsilon)p(y \mid x_i) + \varepsilon u(y \mid x_i)]\log q_\theta(y \mid x_i)$$

Or, $$L' = \sum_{i=1}^{n}\left\{(1-\varepsilon)\left[-\sum_{y=1}^{K} p(y \mid x_i)\log q_\theta(y \mid x_i)\right] + \varepsilon\left[-\sum_{y=1}^{K} u(y \mid x_i)\log q_\theta(y \mid x_i)\right]\right\} = \sum_{i=1}^{n}[(1-\varepsilon)H_i(p, q_\theta) + \varepsilon H_i(u, q_\theta)].$$

One can see that for each example in the training dataset, the loss contribution is a mixture of the cross entropy between the one-hot encoded distribution and the predicted distribution $H_i(p,q\theta)$, and the cross entropy between the noise distribution and the predicted distribution $H_i(u,q\theta)$. During training, if the model learns to predict the distribution confidently, $H_i(p,q\theta)$ will go close to zero, but $H_i(u,q\theta)$ will increase dramatically. Therefore, with label smoothing, one introduces a regularizer $H_i(u,q\theta)$ to prevent the model from predicting too confidently.

In some embodiments, label smoothing is used when the loss function is cross entropy, and the model applies the softmax function to the penultimate layer's log it vectors z to compute its output probabilities p. Label smoothing is a regularization technique for classification problems to prevent the model from predicting the labels too confidently during training and generalizing poorly. See, for example, https://leimao.github.io/blog/Label-Smoothing/.

In some embodiments, both a regression algorithm and a classification algorithm are used to predict pharmaceutical usage and/or time since previous use. For example, Image Analysis Logic 130 can include two separate neural networks, one configured to apply the regression algorithm (that outputs a range) and the other configured to apply the classification algorithm. In this case, the classification algorithm may be applied before the regression algorithm and the regression algorithm is optionally applied separately to each class.

Alternatively, both the regression algorithm and the classification algorithm may be applied by the same neural network. In such embodiments, the neural network is trained to produce both a classification and a regression-based prediction, both of which are quantitative. A regression algorithm outputs one or more values for each percentile chosen. For example, some embodiments use 10%, 25%, 50%, 75%, 90% percentiles for outputs (which represent percentiles of a quantitative prediction), and each of these percentiles may be associated with a probability and/or a confidence measure. From a set of image inputs, the neural network of Image Analysis Logic 130 typically generates one or more values for each percentile chosen. Multiple outputs from distinct algorithms may be used to confirm a determination of environmental exposure and/or environmental exposure time and/or dosage. This scenario is optionally used to establish confidence in the overall prediction since the regression and classification algorithms should produce the same result.

Image Analysis Logic 130 may employ other machine learning algorithms or combinations thereof, in addition to or as an alternative to regression and classification. For example, Image Analysis Logic 130 may be configured to apply a regression that outputs an estimated range, a range being more accurate and/or useful than single point predictions. However, single point predictions can be used if many neural networks are generated (each trained on a different subset of the images/data) from different subsets of the data, which are then statistically analyzed to form an average and/or distribution. In some embodiments, a Bayesian neural network is used to capture the epistemic uncertainty, which is the uncertainty about the model fitness due to limited training data. Specifically, instead of learning specific weight (and bias) values in the neural network, the Bayesian approach learns weight distributions, from which it samples to produce an output for a given input, to encode weight uncertainty. Bayesian networks can also be used in a similar fashion in the classification approaches to prediction discussed herein.

As previously highlighted, Image Analysis Logic 130 can be configured, employing the aforementioned algorithmic and machine learning techniques, to discern whether a particular pharmaceutical or a class of pharmaceuticals is either currently in use or has been utilized by the patient. This determination extends to encompass a multitude of facets, including the likelihood of pharmaceutical consumption, the current dosage (or a dosage range), whether the prescribed dosage aligns with the patient's body weight, and various other clinical parameters that are integral to establishing an appropriate dosage regimen. These assessments are grounded in the comprehensive analysis of ultrasound images, potentially complemented by additional patient-related factors. For instance, Image Analysis Logic 130 may be tailored to derive the aforementioned evaluations from clinical data. This clinical dataset might encompass a range of variables, such as genetics, body weight, patient medical history, blood glucose levels, heart functionality, kidney performance, blood pressure readings, infection status, nutritional profiles, substance use (including smoking and alcohol consumption habits), patient age, socioeconomic status, living environment, income levels, and even ancestral background. Image Analysis Logic 130 can be strategically configured to accept any singular element from this clinical dataset or combine multiple factors to generate the estimates and determinations discussed herein, partly predicated on this clinical information.

Optionally, Determination System 100 integrates Calculation Logic 140, designed to derive outputs based on the estimates generated by Image Analysis Logic 130. For instance, Calculation Logic 140 can be programmed to compute a dosage range, alongside an estimate of the duration for which the determined dosage level has been used. Calculation Logic 140 may achieve this by calculating a dosage or dosage range through the utilization of a probability distribution, represented, for instance, in percentiles. Furthermore, Calculation Logic 140 can ascertain the probability of prior pharmaceutical usage by employing a distribution function on the estimates provided by Image Analysis Logic 130 and subsequently generating a probability distribution based on this data. In certain embodiments, Image Analysis Logic 130 is equipped to generate specific characteristics associated with this distribution function. For example, in select instances, an estimation of dosage reliability can be factored into the determination, allowing for the calculation of a width parameter (e.g., standard deviation) of the distribution function. It's important to note that Calculation Logic 140 may be integrated within Image Analysis Logic 110, offering an alternative approach to processing and analysis.

Determination System 100 optionally further includes a User Interface 150 configured to provide to a user estimates and/or determinations made using Image Analysis Logic 130. User Interface 150 optionally includes a graphical user interface (and the logic associated therewith) and may be displayed on an instance of Image Generator 110, a mobile device (in which case User Interface 150 can include a mobile app.) or on a computing device remote from Image Generator 110 and/or Image Analysis Logic 130. For example, User Interface 150 may be configured to display at least one or two of: current pharmaceutical usage, the estimated dosage, previous pharmaceutical usage, an estimated time range for the previous pharmaceutical usage, and the determination of a proper dosage based on patient characteristics. In some embodiments, User Interface 150 is configured for a remote user to upload one or more ultrasound images for processing by Image Analysis Logic 130.

As is discussed further herein, in some embodiments, User Interface 150 is configured to provide feedback to a user in real-time. For example, User Interface 150 may be used to give instructions to an ultrasound technician during an ultrasound session, to generate images which result in a better determination and/or an estimate related to previous and current pharmaceutical usage and dosage.

Determination System 100 optionally further includes a Data Input 160 configured to receive data regarding a patient, e.g., clinical data regarding the patient. Data Input 160 is optionally configured to receive any of the clinical data discussed herein, which may be used by Image Analysis Logic 130 to generate the estimates and/or probabilities discussed herein. For example, this data can include any of the clinical data discussed herein, or inputs from a user of Image Generator 110. In some embodiments, Data Input 160 is configured to receive medical images, such as ultrasound images, from remote sources.

Determination System 100 optionally further includes Feedback Logic 170. Feedback Logic 170 is configured to guide acquisition of ultrasound images based on a quality of the estimate and/or determinations related to the patient. For example, if analysis of ultrasound images, using Image Analysis Logic 130, obtained during an imaging session, results in determinations and/or estimates having inadequate precision, accuracy, and/or reliability, then Feedback Logic 170 may use User Interface 150 to inform a user that additional ultrasound images are desirable.

Further, in some embodiments, feedback logic is configured to direct a user to obtain ultrasound images of specific features such as motion of a heartbeat, heart rate, the liver, the kidneys, blood flow, bone development, spine, capillary perfusion, uterus, ovaries, testicles, femur, humerus, endometrium, endometrium vascularization, the adnexa, and/or the like. In some embodiments, Image Analysis Logic 130 is configured to classify ultrasound images according to subject matter and/or objects included within the images. For example, separate subject matter classes may include any of the views and/or features discussed herein. In such embodiments, Image Analysis Logic 130 may be configured to identify objects in the ultrasound images and determine that there are sufficient quality images of objects in each subject matter classification. (Subject matter classification is not to be confused with classification of ultrasound images according to a class of pharmaceutical usage or dosage.) If there are not sufficient images, then the User Interface 150 may be used to request that the operator of Image Generator 110 obtain additional images including the additional objects. Feedback Logic 170, thus, may be configured to indicate a need to acquire additional ultrasound images useful in the estimation that the patient is currently using a pharmaceutical. In a specific example, Image Analysis Logic 130 may be configured to request at least one set of images indicative of pharmaceutical dosage and at least one set of images indicative of previous pharmaceutical usage and dosage. In some instances, Feedback Logic 270 is configured to guide the positioning of the image generator (e.g., an ultrasound head) so as to generate images that are more useful in the estimation that the patient has been, or is currently using, a pharmaceutical. Such guidance may include positioning of an ultrasound probe in a specific position or a written/audio request such as "obtain images showing entire kidney."

In various embodiments, Feedback Logic 170 is configured to guide or request acquisition of new images that would be beneficial to training future models to obtain greater accuracy.

Determination System 100 optionally further includes Training Logic 180. Training Logic 180 is configured for training Image Analysis Logic 130, Feedback Logic 170, Image Acquisition Logic 190, and/or any other machine learning system discussed herein. Such training is typically directed at the end goal of learning to make quantitative determinations and/or estimates relating to a patient's previous or current pharmaceutical usage or dosage. For example, Training Logic 180 may be configured to train Image Analysis Logic 130 to make a quantitative determination and/or estimate of the dosage of a pharmaceutical. As described elsewhere herein, this determination may be made using both a quantile regression algorithm and a classification algorithm, together or separately.

While Training Logic 180 may use any applicable selections of the commonly known neural network training algorithms, Training Logic 180 optionally includes a variety of improvements to better train the neural networks disclosed herein. For example, in some embodiments Training Logic 180 is configured to pretrain a neural network of Image Analysis Logic 130 to better recognize features in ultrasound images. This pretraining can include training on images with varying orientation, contrast, resolution, point of view, etc., and can be directed at recognizing anatomical features within the ultrasound images. Pretraining is optionally performed using unlabeled data.

In some embodiments, Training Logic 180 is configured to generate additional training images, in cases where training images for a specific condition are sparse or infrequent. For example, once it is known which images and features are most predictive, Training Logic 180 can take subsets of the images, and use a GAN (Generative Adversarial Network) to generate new training images including the features that predict the use of rare pharmaceuticals.

In some embodiments, Training Logic 180 is configured to train on multiple sets of images, the images optionally being from different patients. By training on multiple sets of images, rather than on single images, overfitting of the data can be reduced. Preferably, each of the sets is large enough to assure that there are at least some images within the set including information useful for making the quantitative determinations discussed herein.

In some embodiments, Training Logic 180 is configured to train Image Analysis Logic 130 to enhance images. For example, Image Analysis Logic 130 may be pretrained to enhance poor quality ultrasound images, or to reveal features, such as capillary perfusion and/or vascularization, that would not normally be visible in the ultrasound images being processed. Such enhancement may allow the use of a handheld ultrasound image to generate the images processed to make quantitative determinations related to current or previous pharmaceutical usage or dosage.

In some embodiments, Training Logic 180 is configured to train neural networks in multiple stages, e.g., as in transfer learning. For example, a neural network may first be trained to recognize relevant patient features, then be trained to estimate current or previous pharmaceutical usage or dosage, and then be trained to provide a quantitative estimate of the length of time of current or previous pharmaceutical usage.

Determination System 100 typically further includes a Microprocessor 195 configured to execute some or all of the logic described herein. For example, Microprocessor 195 may be configured to execute parts of Image Analysis Logic 130, Calculation Logic 140, Feedback Logic 170, Training Logic 180, and/or Image Acquisition Logic 190. Microprocessor 195 may include circuits and/or optical components configured to perform these functions.

Figure 2:
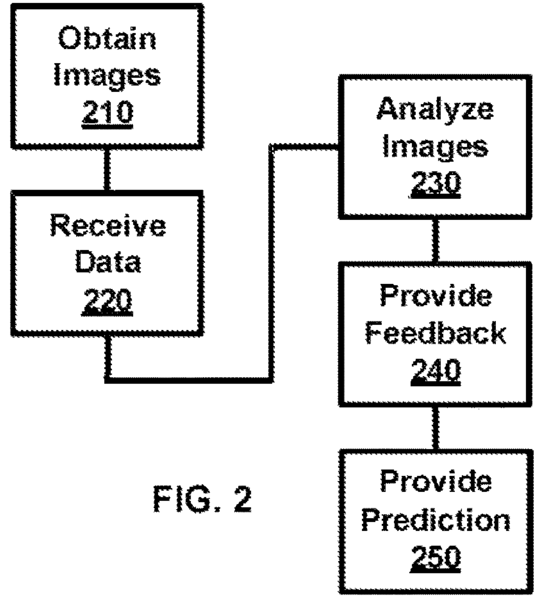
FIG. 2 illustrates methods of making a quantitative determination according to various embodiments of the invention.

FIG. 2 illustrates methods of making a quantitative (optionally medical) determination, according to various embodiments of the invention. A quantitative determination is optionally used to provide specific dosage adjustment suggestions to enable proper dosage for use. As such, the methods of FIG. 2 are optionally followed by appropriate dosage or exposure adjustment.

In an Obtain Images Step 210, a set of one or more images are obtained. These images are typically related to a specific patient. These images may be obtained from a source external to Determination System 100 or may be obtained using Image Generator 110. For example, in some embodiments, ultrasound images are uploaded to Storage 120 via a computer network such as the internet. Images may be received from an electronic medical records system. In other embodiments, images are generated using a medical imaging system such as any of those discussed herein. The images are optionally stored in Storage 120. The images can include any combination of the views and/or features discussed herein and are optionally classified based on their respective views and features (subject matter classification).

In an optional Receive Data Step 220, additional clinical data regarding the patient is received. Again, this data may be received from an electronic medical records system, provided by the patient, and/or provided by a caregiver. The received clinical data can include any of the clinical data discussed herein and is optionally received via Data Input 160.

In an Analyze Images Step 230 the images obtained in Obtain Images Step 210 are analyzed using Image Analysis Logic 130. The images are analyzed to produce one or more quantitative or qualitative determinations. For example, a quantitative determination can include an estimate of a current (at the time the images were recorded) dosage of a chemical compound, or an estimate of a time the compound has been used by the patient. The determination is a "quantitative determination" as defined elsewhere herein. In addition to the images, the quantitative determination is optionally further based on the clinical data received in Receive Data Step 220. The methods of analysis in Analyze Images Step 230 can include any combination of the algorithms and/or machine learning systems discussed elsewhere herein, including those discussed with reference to Image Analysis Logic 130. For example, analyzing medical images can include using a quantile regression algorithm and/or a classification algorithm to make a quantitative determination relating to current or previous chemical compound usage or dosage. In another example, analyzing the medical images includes using a regression algorithm to provide an estimate that a chemical compound has been currently used for a specific timeframe, and optionally to estimate the time of a previous usage of a chemical compound, the regression algorithm being configured to determine an estimated time of current pharmaceutical usage into one or multiple time ranges.

In an optional Provide Feedback Step 240, a user (e.g., a caregiver, or possibly the patient) is provided with feedback regarding acquisition of the images. This feedback can be based on, for example, a quality of the quantitative determination and/or a classification of images already acquired. In specific examples, during an ultrasound session, a caregiver may be asked to acquire additional images of different resolution, of different views, of different features, and/or the like. Obtain Images Step 210 and Analyze Images Step 230 are optionally repeated following Provide Feedback Step 240.

In a Provide Determination Step 250 the quantitative or qualitative determination(s) generated in Analyze Images Step 230 is provided to a user, e.g., a patient or caregiver. The determinations are optionally also placed in Storage 120 and/or an electronic medical records (EMR) system. In various embodiments, the determinations are provided via a web interface, via the EMR system, via a mobile application, on a display of Image Generator 110, on a display of a computing device, and/or the like.

Figure 3:
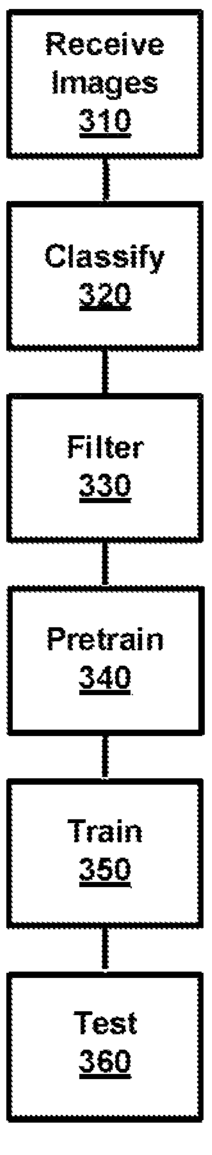
FIG. 3 illustrates methods of training a medical diagnostic system according to various embodiments of the invention.

FIG. 3 illustrates methods of training a medical determination system, according to various embodiments of the invention. The methods illustrated by FIG. 3 are optionally used to train Image Analysis Logic 130, Feedback Logic 170, and/or Image Acquisition Logic 190. The methods may be performed using Training Logic 180.

In a Receive Images Step 310, a plurality of medical images are received as a training set. The received medical images optionally include ultrasound images of a patient before or after a pharmaceutical is administered to provide a means of calibration for an individual patient. The received images are optionally stored in Storage 120.

In an optional Classify Step 320, the received images are classified according to the views or features included within the images. For example, an image may be classified as showing the heart or classified as showing the liver. Classify Step 320 is optionally performed by a neural network included in Image Analysis Logic 130 and/or trained by Training Logic 180. Classify Step 320 may also include classifying images according to (actual or estimated) current or previous chemical compound dosage or usage, and/or a known outcome of their respective pharmaceutical usage. For example, images may be classified as having been generated at a specific dosage of a specific pharmaceutical. It should be noted that as used herein, "neural network" specifically excludes organic brains.

In an optional Filter Step 330, the received images are filtered. Filtering can include removing images that lack features or views that have been determined to have little or no determinative value. For example, a class of images of a bladder may be determined to have little value in determining a quantitative or qualitative determination, and this class of images may be removed from the training set. Images may also be filtered according to their quality or resolution, etc.

In some embodiments, Filter Step 330 includes balancing of a number of images in various classes. For example, for training purposes, it may be desirable to have roughly equal numbers of extremely rare chemical compounds, unusual dosages, off-label use of a pharmaceutical compound, and unusual environmental exposure of a chemical compound or poison. Specifically, balancing may be used to adjust quantities of the images based on dosage. Likewise, for training purposes, it may be desirable to balance numbers of images within the training set based on classification of views and/or features as determined in Classify Step 320.

In an optional Pretrain Step 340, the neural network is optionally pretrained to recognize features within the images or types of images. For example, a neural network within Image Analysis Logic 130 may be pretrained to recognize features in ultrasound images of varying orientation, resolution, and/or quality.

In a Train Step 350, the neural network is trained to provide a quantitative or qualitative determination regarding current or previous chemical compound usage or dosage. As discussed elsewhere herein, the quantitative determination can include an estimate of a dosage, an estimate of a time since a previous usage, and/or an estimate of current usage time or exposure.

In an optional Test Step 360, determinations made by the neural network trained in Train Step 350 are tested using test images. This testing may be performed to determine the accuracy and/or precision of the quantitative or qualitative determinations generated by the neural network.

The quantitative or qualitative determination of a current or previous usage of a chemical compound is optionally used to selectively select a population for a clinical trial. For example, assuming that the exposure to a particular chemical compound occurs in less than 1% of patients, it would be inefficient to give a general population of patients a candidate therapy in order to detect a benefit to the unidentified 1% of patients. However, by identifying the 1% of the patients most likely to result in the exposure to the rare compound a study can be made of the benefit seen within this population for a candidate therapy. Such a study is much more efficient and more likely to reveal benefits with better statistical relevance. The systems and methods disclosed herein may be used to identify such preferred populations for clinical studies. This approach is particularly beneficial for conditions that begin development (and could benefit from therapy) well before clear symptoms appear, e.g., asbestos or lead.

The various methods illustrated in FIGS. 2 and 3 are optionally used in combination and are optionally performed using the systems illustrated by FIG. 1. For example, the methods of FIGS. 2 and 3 may be used together.

It should be understood that the present invention is not limited to only pharmaceutical compounds to treat disease, methods described herein can be used for identifying what compound a person may have unknowingly taken such as in the case of an accidental poisoning, or for identifying a prolonged exposure to toxic environmental substances such as asbestos or lead. In addition to determining exposures to substances like poisons and toxins, the present invention can also be utilized to determine deficiencies in a person such as vitamin deficiencies, hormone imbalances, illnesses, and infections. Those of ordinary skill will be able to identify still other conditions that AI can be trained to determine. This invention can also be used to calibrate an optimum pharmaceutical dosage for an individual patient as well as a means of calibrating the determinations based on the uniqueness of individuals. These steps may also be used to determine "effective dosage" for specific patients due to conditions that may prevent or accelerate absorption of a chemical compound into the body. Also, a compound class could be determined by the effect it has on the human body and not based on similarity of chemical structure or properties. For example, it could be determined that a patient is using a carcinogen whether known or unknown even though carcinogens cover a wide variety of chemical compounds that may have little or no similarity in chemical properties or structure.

Example

The following is an illustrative example, which may be included in any of the embodiments discussed herein:

All ultrasounds from any patient are used to train the neural networks discussed herein. However, different models can be created for different chemical compounds or classes of chemical compounds.

Note: The following models are simply individual embodiments that show how to create a working model. Many of the hyperparameters such as the learning rate, batch size, and number of epochs can be adjusted without issue.

A machine learning algorithm (the code), set forth below, was created and used to train a neural network to make determinations whether a patient had taken the drug progesterone, based on ultrasound images acquired from the patient. Both transformer and CNN architectures were successfully used. The training was conducted using a dataset of ultrasound images, totaling 1.8 million images labeled with whether the patient was on the drug progesterone, or not, at the time the ultrasound image was acquired. The dataset representing 21,254 people, of which 16,640 images were labeled as positive for progesterone use. The images were acquired of all anatomical areas of female reproductive anatomy. The dataset was split into a training set and a validation set. Ten percent of patients were selected randomly to comprise the validation set, the remaining images comprised the training set. Next, using the labeled data in the training set, the algorithm gradually learned to extract relevant features from these images, such as anatomical structures that may be different depending on progesterone use, but not necessarily visible to the human eye. For progesterone, the relevant anatomical structures were found to be primarily the ovaries, adnexa, uterus, cervix and placenta, however this list is not exhaustive. During the training session the algorithm was repeatedly tested against the validation set which does not participate in the training. The algorithm's performance was evaluated on the validation set of ultrasound images that had not been used for training, and the algorithm's predictions were compared against the actual labels. The training was halted once the validation accuracy began to decrease after reaching a peak accuracy, indicating the algorithm was likely no longer learning generalized features, but more likely memorizing features of the training set. The algorithm proved accurate on the validation data, yielding a prediction rate of 89%, and was therefore ready to be deployed for use on images of anatomy that are affected in some physiological way by the use of the drug progesterone and not part of the initial training dataset.

Import all the Libraries Used in the Code from fastai.vision.all import*

Any imaging study where the patient was taking progesterone at the time of the imaging study can be labeled "Progesterone Use", or "None" if patient was not taking progesterone at time of the imaging study. However, this labeling is not strictly necessary; other classification labels may be used.

The following path is a folder containing one subfolder for each class to be predicted which are "Progesterone Use" or "None". This is only one embodiment; any number of different classifications would also work. For example, there may be two, three, four or more classes. For example "Previous Progesterone Use" could be added.

Progesterone use is about 1% of the total dataset used, however training may be more effective when using a balanced dataset which is the case here. The validation set is not balanced in this embodiment which reflects the accuracy of the distribution in the real world, but could be balanced in other embodiments. In some embodiments the neural network has an equal chance of being fed an instance of one of the categories. In various embodiments, at least 50% or 75% of the training set includes images balanced among the possible classes.

A large dataset containing over 1.8 million ultrasound images with annotations about the patient's environment was used for the training and validation of this invention. Optionally, the image size can be set to 400 by 400 pixels. Most of the images in this dataset are several times this size and are reduced in size for training and inference efficiency. Accuracy can increase with increasing image size, however there can be diminishing returns. Alternative embodiments use images of at least 224×224 pixels, 640×640 pixels, or 2048×2048 pixels, or any range therebetween.

This will create an object to feed data to the neural network during training and validation. In this example, 10% of the studies are put into a validation set which is used to monitor training. The validation set contains the same distribution of progesterone use that exists in the original dataset. The data is balanced for training; however, the validation set is the natural distribution and not balanced in any way. The batch size is arbitrarily set to 48 images but can be adjusted if necessary. Adding the function aug_transforms causes each image to be randomly augmented which can reduce overfitting. Examples of augmentation include but are not limited to adjusting brightness, contrast, and flipping the image horizontally. This embodiment uses Cross Entropy as the loss function and it is training as a label classification problem where there is exactly one label for each image. Other embodiments could use other loss functions such as mean squared error if the data is viewed as a regression problem.

```
from fastai.vision.all import *
def multi_1(x):
  return [1]
# Define data transformations
tfms = aug_transforms( )
image_size = 400
# Get image file names from the specified path
fnames = get_image_files(path)
# Create a DataBlock for label classification
dblock = DataBlock(
  blocks=(ImageBlock, CategoryBlock),
  get_items=get_image_files,
  get_y=Pipeline([parent_label, multi_1]),
  splitter=GrandparentSplitter( ),
  item_tfms=Resize(image_size),
  batch_tfms=[*tfms])
# Create DataLoader
dls = dblock.dataloaders(path, bs=48)
```

Create an object which will control training and inference at a high level. Using a high value for weight decay is one example. Other forms of regularization of the weight values may have similar effects.

Obtain a pretrained network for use in transfer learning, however training a neural network from an initial randomized form will also work. In this case ResNet-152 is used. Other variations of resnet will work and the more layers the better the accuracy. Many other neural networks will also give usable results. The example below illustrates an example of training. The parameters and steps may be varied in alternative embodiments.

Create a learner object with a CNN architecture (however vision transformers may also be used)

```
learn = cnn_learner(dls,
  resnet152,
  cbs=[ShowGraphCallback( )],
  wd=0.1,
  metrics=[accuracy],
  loss_func=CrossEntropyWithLogitsLossFlat( ))
```

This will freeze the parameters of the convolutional part of the neural network and will allow training of just the linear layers. Other embodiments will not necessarily require the step of freezing layers.

learn.freeze( )

Train the neural network for 10 epochs while gradually increasing then decreasing the learning rate with a scheduler. The maximum learning rate will be 1e-3. Other embodiments may use an alternative training schedule.

learn.fit_one_cycle(10, 1e-3)

This will allow the entire neural network to be trained including the convolutional layers.

learn.unfreeze( )

Further train the neural network for 5 epochs while gradually increasing then decreasing the learning rate with a scheduler. The maximum learning rate will be 1e-5.

learn.fit_one_cycle(5, 1e-5)

Further train the neural network for 5 epochs while gradually increasing then decreasing the learning rate with a scheduler. The maximum learning rate will be 1e-5.

learn.fit_one_cycle(5, 1e-5)

Best validation accuracy of this embodiment is 89%.

This network allows for the identification of the specific anatomical views of the study that are most useful for making this determination. Specific anatomical views or any other information fed to the network can be excluded if it is commonly uninformative, or the various views can be weighted in calculating the final determination.

Each determination outputs a score of how confident the model is which can be used in real time on the ultrasound machine to inform the ultrasound technician when a view which will improve accuracy has been obtained, or the software can automatically capture high confidence views as they are found with no effort from the technician required. This technique can be used to create training sets for continuous improvements in updated models which is a feedback loop for capturing better data for training future models.

The trained system is optionally used to provide an ultrasound technician with real-time feedback. For example, the system may inform the technician when images expected to be the most predictive have or have not been obtained. The system can request that the technician obtain images of specific anatomy of the patient. When an obtained image is identified as being determinative of a progesterone use, the system may request that the technician obtain additional images to confirm or negate the determination of progesterone use. For example, if an image of one part of the anatomy (e.g., a heart) determines progesterone use the system may request that the technician obtain further images of that anatomy or further images of another part of the patient's anatomy (e.g., cervix or uterus).

Making determinations based on individual ultrasounds and then aggregating these individual determinations can be useful in itself, but the method can also be improved upon. One concern with this method is that within a single ultrasound recording session some ultrasound images may show a confident progesterone use while ultrasound images of another part of the anatomy will confidently determine no progesterone use, making a simple aggregation less effective. Accordingly, neural networks have been created that allow multiple images to be classified in a single pass through a neural network or sequence of networks. As the number of images simultaneously fed into a neural network increases, the accuracy also typically increases. Therefore, more efficient methods of passing (in parallel, or sequentially) multiple images through a single network (or sequence of networks) were developed.

This does not necessarily have to be a classification problem. The values to determine could be numeric values representing the desired target and a neural network to perform a regression is created instead.

Training data can be created by training a neural network to modify images from one class into another if the data is limited for a particular class. An example of a neural network which can convert images from one class to another is a cyclegan.

It is not necessary for images to be used. The underlying sound waves captured by the ultrasound machine before conversion into an image could also be used as an alternative to or in addition to images for this determination.

Transformer Aggregation Architecture

A neural network can be created which can extract the useful information from each image which is then aggregated using multiple neural networks combined into a single neural network using a transformer style architecture, however these networks could be separate in other embodiments. An ultrasound session is one in which a technician takes a set of images in one interaction with a patient. Considering many ultrasound sessions exceed 100 images this is useful for processing efficiency and accuracy. Transformers can be applied to sequential (or time series) data where data points are correlated in a sequence. The ultrasound images in an ultrasound session don't have a significant amount of order to them, if any, however this type of network can carry information from a previous step of processing a single image forward and this combined information can be classified after each image in an ultrasound session is processed. Ultrasound sessions do not have a significant amount of order because an ultrasound technician typically jumps from viewing one anatomical feature to another anatomical feature. It is possible to record a video of the entire session and in these embodiments the images in the video have a sequential nature and this general technique can be employed.

```
from fastai.vision.all import*
from pathlib import Path
```

Get the data which is divided into training, validation, and test sets. The training data is created in an unusual way. Instead of just using each study as a separate folder of images, folders are created which randomly sample a range of images from pools of all progesterone use and non-use studies. It is also possible to sample images from a pool of each class of the desired sequence length at run time. Other embodiments use 2, 3 or more classes or numeric values. There are a few reasons to do this.

First, some patients may not be forthcoming in their compliance of progesterone use, which means the training data can contain a significant number of mislabeled studies. Second, the patient may be inadvertently using the progesterone incorrectly. By taking a random selection it makes it possible for each training sample to have some ultrasounds which contain the needed information to make a correct determination.

It should also be noted that multiple ultrasound sessions are commonly performed on a single pregnancy. Multiple sessions from a single pregnancy could also be combined when performing a determination of progesterone use across the prescribed use time span.

A single session may indicate progesterone use but may not have a high confidence. Therefore, the system may indicate that a follow up session is desired and potentially when the follow up session should be conducted.

Data Acquisition

To obtain the paths to folders containing images from individual studies, the following function can be used:

```
def get_sequence_paths(path):
    sequence_paths = [ ]
    for folder in path.ls( ):
        for c in folder.ls( ):
            sequence_paths += c.ls( )
    return sequence_paths
folders = get_sequence_paths(IMAGES_PATH)
```

In this example, the sequence length is set to 36 images, but a smaller or larger range can be used. More images may improve results, but there can be diminishing returns. The image size used here is 400×400 pixels, which is larger than the typical 224×224 pixels used in image classification problems. However, smaller or larger images can also be utilized:

seq_len=36 image_size=400

A custom ImageTuple class is defined to handle image sequences and display them:

```
class ImageTuple(Tuple):
  def show(self, ctx=None, ** kwargs):
    n = len(self)
    img0, img1, img2 = self[0], self[n//2], self[n-2]
    if not isinstance(img1, Tensor):
      t0, t1, t2 = tensor(img0), tensor(img1), tensor(img2)
      t0, t1, t2 = t0.permute(2, 0, 1), t1.permute(2, 0, 1),
      t2.permute(2, 0, 1)
    else:
      t0, t1, t2 = img0, img1, img2
    return show_image(torch.cat([t0, t1, t2],
    dim=2), ctx=ctx, ** kwargs)
```

An ImageTupleTransform is also created to encode images into tuples for our dataset: class ImageTupleTransform(Transform):

```
    def_init_(self, seq_len=36):
      self.seq_len = seq_len
    def encodes(self, path):
```

-continued

```
        images = path.ls( )
        return ImageTuple(tuple(PILImage.create(f)
        for f in L(random.choices(list(images),
    k=self.seq_len)) if os.path.isfile(f)))
    tfms = aug_transforms(flip_vert=False)
    grandparent_splitter = GrandparentSplitter( )(files)
    itfm = ImageTupleTransform(seq_len=seq_len)
    ds = Datasets(files, tfms=[[itfm], [parent_label, Categorize]],
    splits=grandparent_splitter)
    dls = ds.dataloaders(bs=bs, after_item=[Resize(image_size),
    ToTensor], after_batch=[*tfms,
    IntToFloatTensor], drop_last=True)
    Encoder Class
```

The Encoder class loads a model pretrained on single ultrasound images, removes the final classification layer, and returns 512 features for each image:

```
class Encoder(Module):
  def_init_(self, **kwargs):
    model = load_learner("davit_large").model
    self.body = model[0]
    self.head = model[1][:-4]
  def forward(self, x):
    return self.head(self.body(x))
```

This class allows features to be extracted from images using a pretrained model. The number of features can be adjusted as needed for specific use cases.

The following module takes the features from each image and classifies the entire sequence of images.

```
import torch
import torch.nn as nn
import torch.nn.functional as F
class TransformerEncoder(Module):
  def_init_(self, num_classes=2, d_model=512, nhead=8,
num_encoder_layers=6, dim_feedforward=2048, dropout=0.1):
    self.transformer_encoder = nn. TransformerEncoder(
      nn.TransformerEncoderLayer(d_model, nhead,
      dim_feedforward, dropout), num_encoder_layers
    )
    self.fc = nn.Sequential(
      nn.Linear(d_model, num_classes),
    )
  def forward(self, x):
    x = self.transformer_encoder(x)
    x=x.mean(dim=1) # Pooling operation, you can replace
this with another method if needed
    x = self.fc(x)
    return x
Example usage:
dls_c = 2
model = TransformerEncoder(num_classes=dls_c, d_model=512,
nhead=8, num_encoder_layers=6, dim_feedforward=2048, dropout=0.1)
```

Create a Learner object which will control training and inference at a high level. Using a high value for weight decay is helpful in making a correct determination.

GradientAccumulation can be used if GPU memory constraints require it. This will accumulate gradients for 32 items before making an update to the weights of the network.

```
import torch.nn as nn
from fastai.learner import cnn_learner, Learner
from fastai.vision.all import ShowGraphCallback,
GradientAccumulation, SaveModelCallback class
TransformerModel(nn.Module):
```

-continued

```
  def_init_(self, num_classes, d_model=512, nhead=8,
num_encoder_layers=6, dim_feedforward=2048, dropout=0.1):
    # transformer architecture here
  def forward(self, x):
    # Forward pass through the transformer
# Custom splitter function to separate transformer
encoder from other layers def transformer_splitter(model):
  transformer_layers = [ ]
  other_layers = [ ]
  for name, param in model.named_parameters( ):
    if 'transformer_encoder' in name:
      transformer_layers.append(param)
    else:
      other_layers.append(param)
  return [transformer_layers, other_layers]
# Create your data loaders (dls) here
# Replace 'dls' with the actual data loaders
# Instantiate your TransformerModel
model = TransformerModel(num_classes=dls.c)
# Create a Learner with the model and custom splitter
learn = Learner(dls,
          model,
          wd=0.3,
          metrics=[accuracy],
          cbs=[ShowGraphCallback( ),
          GradientAccumulation( ),
SaveModelCallback(monitor='valid_loss',
fname='Transformer_Model')],
          splitter=transformer_splitter).to_fp16( )
```

Train the neural network for 5 epochs while gradually increasing then decreasing the learning rate with a scheduler. The maximum learning rate will be 1e-3. These parameters are simply chosen for this embodiment, many other choices would also work.

learn.freeze( )learn.fit_one_cycle(5, 1e-3)

Alternative Embodiments

To aggregate the individual determinations for a study run each through a tournament to determine final classification.

Reinforcement learning can be used in place of the transformer shown.

Use multiple models trained on different subsets of the data to create ensembles which typically increases accuracy.

Use additional data about the patient in combination with the images such as age or relevant events in the medical history of a patient.

Additional outputs in addition to the chemical compound usage and dosage can be used. Some examples are age, BMI, sex among others. Having multiple outputs for determination can improve the overall accuracy of the determination due to the inherent relationships between the various items being determined. Any of these alternative determinations can be performed without the chemical compound usage or dosage if desired.

The systems and methods disclosed herein have been applied to real world data obtained from a clinical context and have been shown to consistently produce a positive predictive value above 85% and a negative predictive value above 88%.

Several embodiments are specifically illustrated and/or described herein. However, it will be appreciated that modifications and variations are covered by the above teachings and within the scope of the appended claims without departing from the spirit and intended scope thereof. For example, while ultrasound images and chemical compound use are taught herein by way of example, the systems and methods described herein may be applied to other medical information and conditions. Examples, include determination of physical activity, physical or mental stress, sunlight exposure, diet, nutritional deficiencies, sleep deprivation, radiation exposure, and/or any other medical condition the precursors of which may be present in an ultrasound image. The methods and systems disclosed may be used to determine a current clinical state separately or in combination with the (optionally quantitative or qualitative) determination of a future state. The systems and methods disclosed herein may also be used to predict future health conditions of a patient. For example, development of cancer, heart problems, mental health issues, poor function of various organs, and/or the like. It will be understood that the terms "predict" and "determine" are used interchangeably herein.

While the teachings herein include use of medical images, e.g., ultrasound images, in various embodiments, the systems and methods may use raw data other than in the form of images. For example, Image Analysis Logic 130 is optionally trained to process raw ultrasound data rather than or in addition to images generated from such data.

The embodiments discussed herein are illustrative of the present invention. As these embodiments of the present invention are described with reference to illustrations, various modifications or adaptations of the methods and or specific structures described may become apparent to those skilled in the art. All such modifications, adaptations, or variations that rely upon the teachings of the present invention, and through which these teachings have advanced the art, are considered to be within the spirit and scope of the present invention. Hence, these descriptions and drawings should not be considered in a limiting sense, as it is understood that the present invention is in no way limited to only the embodiments illustrated.

The "logic" discussed herein is explicitly defined to include hardware, firmware or software stored on a non-transient computer readable medium, or any combinations thereof. This logic may be implemented in an electronic and/or digital device to produce a special purpose computing system. Any of the systems discussed herein optionally include a microprocessor, including electronic and/or optical circuits, configured to execute any combination of the logic discussed herein. The methods discussed herein optionally include execution of the logic by said microprocessor.

Computing systems and/or logic referred to herein can comprise an integrated circuit, a microprocessor, a personal computer, a server, a distributed computing system, a communication device, a network device, or the like, and various combinations of the same. A computing system or logic may also comprise volatile and/or non-volatile memory such as random-access memory (RAM), dynamic random access memory (DRAM), static random access memory (SRAM), magnetic media, optical media, nano-media, a hard drive, a compact disk, a digital versatile disc (DVD), optical circuits, and/or other devices configured for storing analog or digital information, such as in a database. A computer-readable medium, as used herein, expressly excludes paper. Computer-implemented steps of the methods noted herein can comprise a set of instructions stored on a computer readable medium that when executed cause the computing system to perform the steps. A computing system programmed to perform particular functions pursuant to instructions from program software is a special purpose computing system for performing those particular functions. Data that is manipulated by a special purpose computing system while performing those particular functions is at least electronically saved in buffers of the computing system, physically changing the special purpose computing system from one state to the next with each change to the stored data.

What is claimed is:

1. A system configured to make a medical determination, the system comprising:

a medical image generator configured to acquire non-invasive medical images of a body part of a patient during an imaging session, the medical image generator further configured to adapt generation of the medical images based on feedback received from image analysis logic by fine-tuning at least one of (i) image generation, (ii) focus, or (iii) image processing parameters;

an image storage storing a set of the medical images of the body part of a the patient, the set of medical images having been acquired during the imaging session;

image analysis logic comprising a trained neural network in communication with the image storage and configured to:

(i) process a plurality of the medical images of the set to provide a plurality of image-level determinations indicative of a quantitative estimate of an exposure of the patient to a pharmaceutical, (ii) generate an aggregate determination regarding the quantitative estimate by aggregating the image-level determinations, wherein the aggregating comprises excluding at least one anatomical view or other information that is determined to be commonly uninformative and/or weighting a plurality of anatomical views in calculating the aggregate determination, and (iii) determine a confidence score associated with the aggregate determination;

feedback logic configured, based on the confidence score and/or a classification of medical images already acquired during the imaging session, to guide acquisition of at least one additional medical image during the imaging session via a user interface;

the user interface configured to provide at least the aggregate determination and guidance output by the feedback logic to a user; and a microprocessor configured to execute at least the image analysis logic and the feedback logic.

2. The system of claim 1 wherein the image analysis logic includes first logic configured to analyze the set of medical images to determine a present exposure to the pharmaceutical at the time the set of medical images were acquired.

3. The system of claim 1 wherein the image analysis logic includes second logic configured to determine a timeframe for a prior exposure to the pharmaceutical.

4. The system of claim 1 wherein the image analysis logic is configured to employ a regression algorithm to provide the quantitative estimate as a range.

5. The system of claim 1 wherein the image analysis logic is configured to employ a classification algorithm to provide the quantitative estimate as one of a plurality of categories.

6. The system of claim 1, wherein the quantitative estimate comprises an estimated dosage range of the pharmaceutical expressed in dosage units.

7. The system of claim 1, wherein the quantitative estimate comprises an estimate of a time period during which the pharmaceutical was used by the patient.

8. The system of claim 1 wherein the quantitative estimate comprises an estimated dosage expressed as a measure of the pharmaceutical over a time duration.

9. The system of claim 1 wherein the quantitative estimate is further based on a clinical data set.

10. The system of claim 1, wherein image analysis logic is further configured to determine the confidence score satisfies a threshold condition and, in response, identifying the at least one additional medical image.

11. The system of claim 1, wherein the feedback logic is further configured to guide acquisition of the at least one additional medical image by at least one of: (i) a recommended anatomical view, (ii) a recommended imaging plane, (iii) a recommended probe position, (iv) a recommended timepoint, or (v) a recommended acquisition setting.

12. The system of claim 1, wherein the non-invasive medical images comprise images generated by at least one of ultrasound imaging, magnetic resonance imaging, computed tomography imaging, positron emission tomography imaging, x ray imaging, or optical imaging.

13. The system of claim 1, wherein processing the plurality of the medical images further comprises generating a normalized image tensor comprising at least one of: image normalization, image registration, or image resampling into a standardized resolution.

14. The system of claim 1, wherein the feedback logic is further configured to generate a region-of-interest representation that identifies a target anatomical structure.

15. The system of claim 1, wherein the trained neural network comprises at least one of a convolutional neural network, a transformer network, or an ensemble of neural networks.

16. The system of claim 1, wherein the confidence score comprises at least one of a predictive variance, a confidence interval, or an entropy measure.

17. The system of claim 1, wherein the image analysis logic is further configured to receive at least one additional medical image identified by the feedback logic, and to compute an updated quantitative estimate using the at least one additional medical image.

18. The system of claim 1, wherein the trained neural network was trained using supervised learning on labeled training examples that associate non-invasive medical images with corresponding reference exposure values of the pharmaceutical.

19. A method for training a neural network to make a medical determination, the method comprising:

receiving a set of non-invasive medical images of body parts of a plurality of patients, the medical images tagged with information concerning exposure by the respective patients to a pharmaceutical;

classifying the medical images according to views or features included within the medical images;

filtering the medical images to remove images that lack features or views that have been determined to have little or no determinative value and/or to remove medical images filtered according to quality or resolution;

dividing the set of medical images into a training set and a validation set;

providing the medical images of the training set, and their tags, to a neural network to train the neural network to determine a quantitative exposure of the plurality of patients to the pharmaceutical based on images of the body parts; and providing medical images of a single patient from the validation set to the neural network to make a determination, and comparing the determination to the tags associated with the medical images.

20. The method of claim 19 wherein the non-invasive medical images are ultrasound images.

21. The method of claim 19 further comprising classifying the medical images before providing the medical images of the training set to the neural network.

22. The method of claim 19 further comprising resizing the medical images before providing the medical images of the training set to the neural network.

23. A method for making a medical determination, the method comprising:

during a medical imaging session, generating, using an image generator comprising a source and a detector, a set of non-invasive medical images of a body part of a patient;

storing the set of medical images;

providing a plurality of medical images of the set to a neural network that has been trained to determine, from medical images of the body part, a quantitative estimate of an exposure of the patient to a pharmaceutical;

receiving, from the neural network, a plurality of image-level determinations and a confidence score associated with the determinations;

generating an aggregate determination regarding the quantitative estimate by aggregating the image-level determinations, wherein the aggregating comprises excluding at least one anatomical view or other information that is determined to be commonly uninformative and/or weighting a plurality of anatomical views in calculating the aggregate determination;

when the confidence score indicates inadequate precision, accuracy, and/or reliability, providing feedback during the imaging session via a user interface to guide acquisition of at least one additional medical image and/or to adapt generation of medical images by fine-tuning at least one of (i) image generation, (ii) focus, or (iii) image processing parameters; and providing the aggregate determination regarding the quantitative estimate.

24. The method of claim 23 wherein the non-invasive medical images are ultrasound images.

25. The method of claim 23 wherein the neural network employs a regression algorithm and receiving the plurality of image-level determinations further includes receiving one or more ranges.

26. The method of claim 23 wherein the neural network employs a classification algorithm and receiving the plurality of image-level determinations further includes receiving one of a plurality of categories.

27. The method of claim 23 wherein the quantitative estimate of exposure to the pharmaceutical further comprises an estimate of an effective dosage of the pharmaceutical.

28. The method of claim 23 wherein the quantitative estimate of exposure to the pharmaceutical further comprises a time the pharmaceutical should be used by the patient.

29. The method of claim 23, wherein the quantitative estimate comprises an estimated dosage range of the pharmaceutical expressed in dosage units.

30. The method of claim 23, wherein the quantitative estimate comprises an estimate of a time period during which the pharmaceutical was used by the patient.

31. The method of claim 23 wherein the quantitative estimate comprises an estimated dosage expressed as a measure of the pharmaceutical over a time duration.

32. The method of claim 23 wherein the quantitative estimate is further based on a clinical data set.

* * * * *